(12) United States Patent
Fei

(10) Patent No.: US 7,243,616 B2
(45) Date of Patent: Jul. 17, 2007

(54) MULTIFUNCTIONAL HEALTH PROTECTION DEVICE FOR UDDERS OF COWS

(75) Inventor: Daowei Fei, Zhejiang (CN)

(73) Assignee: Toppor Healthtec, Inc., Ninybo, Zhejiang (CN)

( * ) Notice: Subject to any disclaimer, the term of this patent is extended or adjusted under 35 U.S.C. 154(b) by 0 days.

(21) Appl. No.: 10/561,722

(22) PCT Filed: Jun. 23, 2004

(86) PCT No.: PCT/CN2004/000675

§ 371 (c)(1),
(2), (4) Date: Dec. 20, 2005

(87) PCT Pub. No.: WO2004/112469

PCT Pub. Date: Dec. 29, 2004

(65) Prior Publication Data
US 2006/0185619 A1    Aug. 24, 2006

(30) Foreign Application Priority Data
Jun. 24, 2003  (CN)  ................ 03 2 32495

(51) Int. Cl.
*A01K 15/04* (2006.01)

(52) U.S. Cl. ................. 119/852; 119/14.47; 119/14.48; 119/850

(58) Field of Classification Search ............ 119/14.47, 119/14.48, 850, 852
See application file for complete search history.

(56) References Cited

U.S. PATENT DOCUMENTS 928,080 A * 7/1909 Tatman ..................... 119/852

(Continued)

FOREIGN PATENT DOCUMENTS

CN    B 85204929    8/1986

(Continued)

*Primary Examiner*—Teri Pham Luu
*Assistant Examiner*—Willie Berry, Jr.
(74) *Attorney, Agent, or Firm*—Global IP Services; Tianhua Gu

(57) ABSTRACT

The invention relates to a multifunctional health protection device for udders of cows. The device comprises a brassiere, which is provided at its lower portion with circular openings (5) corresponding to four teats of a cow. The four circular opening (5) are equipped with teat cups (8). There is a hole at the fore end of each teat cup (8). The brassiere is formed by the inner and outer hoods (1, 2). An electrical heater (4) is mounted between the inner and outer hoods (1,2). Permanent magnets, which are winded with coils, are arranged around the outer wall of the inner hood and the circular openings. An electrical vibrator (6) may be provided at the centers of the four circular openings between the inner and outer hoods. A plurality of conductive rubber electrode (7) is mounted on the inner wall of the inner hood. A removable cup (9) for containing sterilizing agent is installed in the brassiere (8). A ring seal (11) with a central hole is provided at the upper part of the removable cup. The device of the invention can implement milking, keeping constant temperature, heating therapy and vibrating massage to cows and has the functions of dredging meridian, harmonizing the flow of Qi and blood, activating blood and resolving stasis, preventing and curing mastitis of cows, enhancing the ability of lactating to increase the milk production of cows and the like.

9 Claims, 1 Drawing Sheet

U.S. PATENT DOCUMENTS 2,953,671 A * 9/1960 Allen et al. .................. 219/528
5,426,925 A * 6/1995 Smargiassi .................. 54/79.1

FOREIGN PATENT DOCUMENTS

| CN | A 1296379 | 5/2001 |
| DE | A 2812027 | 9/1979 |
| SU | A 1690623 | 11/1991 |

* cited by examiner

MULTIFUNCTIONAL HEALTH PROTECTION DEVICE FOR UDDERS OF COWS

TECHNICAL FIELD

The present invention relates to a multifunctional health protection device for udders of cows, belongs to health devices for cows.

BACKGROUND OF THE INVENTION

Milk is a food with all kind of nutrition. However, many cows have mastitis, the rate is high. Normally, milkers use antibiotics for treating mastitis. Therefore, the amount of rudimental antibiotics in milk is considerable. Human drinking milk having the rudimental antibiotics long term will cause accumulation of antibiotics in body, it results human-body physiological disorder and drug resistance to the antibiotics. Consequently, the milk with rudimental antibiotics is a kind of food pollution, which damages human health. To cue the damage from milk with rudimental antibiotics is more difficult than to rule the environment pollution. The best way to deracinate the damage is treating the mastitis by using less or no antibiotics. Thereby, people expect a kind of health protection device for udders of cows to replace the antibiotics for cow's mastitis. Chinese patent No. 85204929 disclosed a "Brassiere Diminishing Inflammation for Cows with Rare-Earth Permanent Magnet", which is a safe, simple and effective tool for treating mastitis, but it has single function only, needs manual operation, operates inconveniently and is not easy to be popularized.

SUMMARY OF THE INVENTION

The purpose of the present invention is to provide a multifunctional health protection device for udders of cows, which possesses functions of dredging meridian, harmonizing and regulating Qi and blood, multifunction and easy operation.

The device comprises a brassiere, which is provided at its lower portion with circular openings positionally corresponding to the teats of a cow. The circular openings are equipped with teat cups. There is a hole at the fore end of each teat cup. Each hole connects with a sucking milk pipe connected to a milk storing bottle. The milk storing bottle connects with an electric vacuum pump through another pipe. The brassiere comprises an outer hood, which enwraps and connects an inner hood. A heater is fixed between the out hood and inner hood. The heater is made from electric heating wire or electric heating layer or electric PCT ceramics heating material. Permanent magnets that are winded with coils are arranged on the back face of the inner hood and around the circular openings. An electrical vibrator is provided at the center of a circle defined by the multiple circular openings and between the inner and outer hoods. Conductive rubber electrodes are mounted on the inner wall of the inner hood. Removable cups for containing sterilizing agent are installed in the teat cups. Ring seals with central hole are provided at the tops of the removable cups, which are located in the teat cups for accommodating medicine or sterilizing liquid.

The multifunctional health protection device for udders of cows of the present invention can implement milking, keeping constant temperature, heating therapy, vibrating massage and pulse alternating magnet therapy to main collateral channels and points. Thereby, the device has functions of dredging meridian, harmonizing and regulating the flow of Qi and blood, activating blood and resolving stasis, preventing and treating mastitis of cows, enhancing the ability of lactating to increase the milk production of cows and the like. The device also greatly decreases the occurring frequency of mastitis and eliminates the side effects of the antibiotics. As a result the hygiene of food and drink is guaranteed.

DETAIL DESCRIPTION OF ILLUSTRATED EMBODIMENTS

Figure 1:
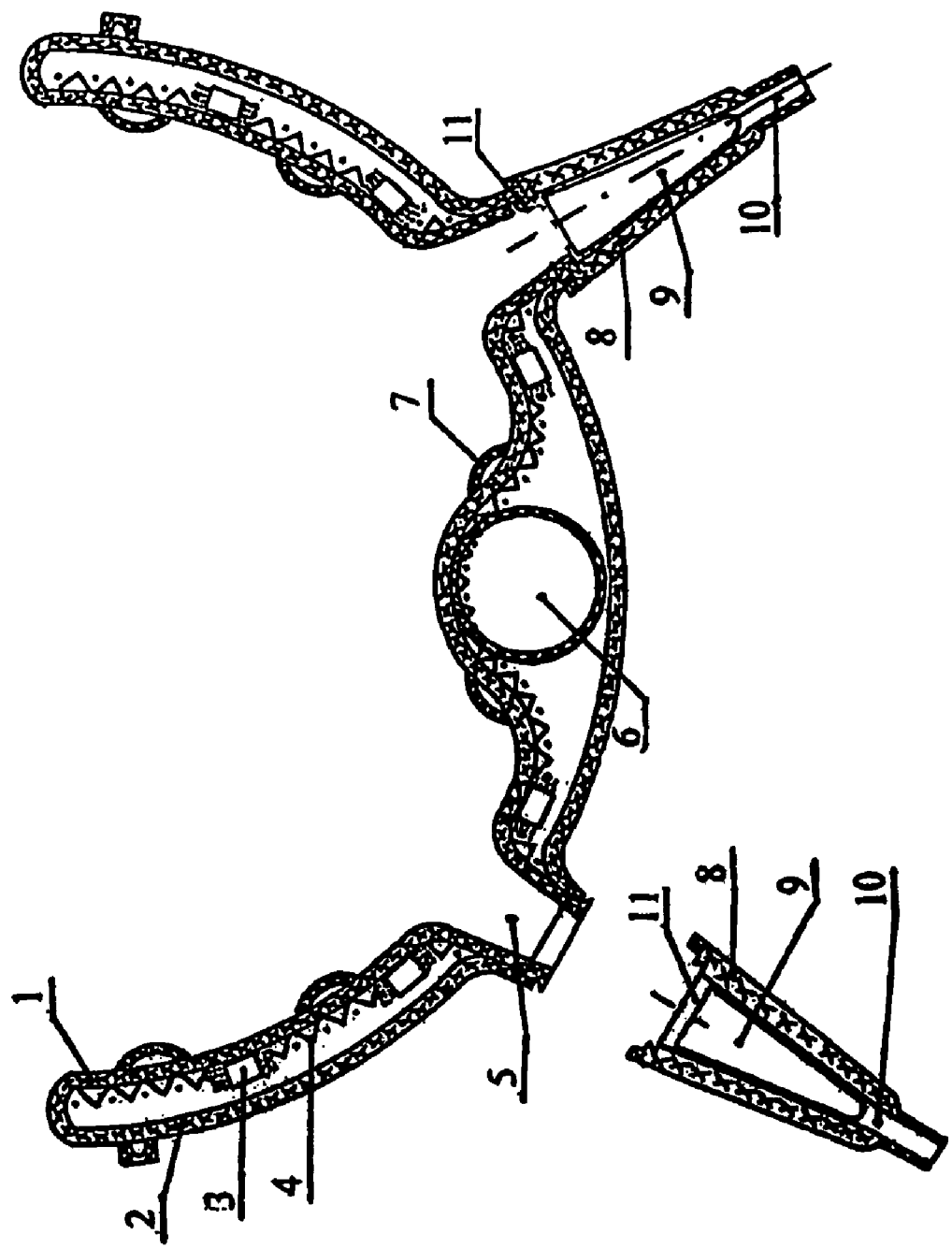
FIG. 1 is an illustration figure for the structure of the multifunctional health protection device for udders of cows of the present invention.

As shown in FIG. 1 the device of present invention comprises a brassiere having U boat shape including an inner hood 1 and an outer hood 2. The outer hood 2 enwraps and connects with the inner hood 1. Four circular openings 5 are provided at the low portion of the brassiere corresponding to the four teats of a cow. The circular openings 5 are equipped with teat cups 8. The teat cup 8 is fastened to the circular opening 5 separably. An electric heater 4 is fixed between the inner hood 1 and outer hood 2. The electric heater 4 is made from electric heating wire or electric heating layer or electric PCT ceramics heating material. Permanent magnets 3 that are wined with coils for creating alternative magnet field are arranged on the inner hood 1. An electrical vibrator 6 is provided at the center of the four circular openings 5 between the inner hood 1 and outer hood 2. Conductive rubber electrodes 7 are mounted on the inner wall of the inner hood 1 for providing electric stimulation to the udders of cows. Removable cups 9 are installed in the teat cups 8. The cup 9 may contain sterilizing agent for eliminating inflammation and treating chap of teat for the udders of cows. Ring seals 11 with central holes made from silicon rubber material are provided on the top of the removable cups 9 in the teat cups 8. There is a hole 10 at the fore end of each teat cup 8, the hole 10 is connected with a milk-sucking pipe (not shown) located in a milk storing bottle (not shown), which is connected with an electric vacuum pump (not shown). The electric heater 4, electric vibrator 6, conductive rubber electrode 7, coil of permanent magnet 3 are connected with an electric controller (not shown) through connecters (not shown) on the outer hood 2.

The operating process is that put the brassiere device on a small vehicle, push the vehicle into the place under the udder of a cow, then raise the brassiere device to cover it on the udder of cow; connect the brassiere device with an electric power; push a button; implement constant heating therapy, vibrating massage therapy and pulse alternating magnet therapy to the main and collateral channels and points. The electric vacuum pump (not shown) make negative pressure on the udder of a cow, which extends galactophore to promote milking and to assist the clogged milk that is filed up in the udder to flow out to the milk storing bottle (not shown) through the milk sucking pipe (not shown).

The device of present invention has functions of dredging meridian, harmonizing and regulating the flow of Qi and blood, defending and treating mastitis for cows and enhancing the Ability for lactating to increase the milk production of cows Although the description above contains many specificities, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A health protection device for udders of cows comprising:
   a brassiere for udders of cows;
   circular openings corresponding to teats of a cow provided on the lower portion of said brassiere;
   teat cups fastened to said circular openings in a separable manner, a hole is at the fore end of each teat cup for connecting with a milk-sucking pipe;
   an inner hood and an outer hood, said brassiere comprises said inner hood and said outer hood, said outer hood enwrapping and connecting with said inner hood;
   a heater located between said inner hood and said outer hood.

2. The health protection device for udders of cows of claim 1, wherein a movable cup is located in said teat cup for containing sterilizing agent, and a ring seal with a central hole is provided on the top of said each removable cup.

3. The health protection device for udders of cows of claim 1 or 2 wherein conductive rubber electrodes are mounted on the inner wall of said inner hood.

4. The health protection device for udders of cows of claim 1 or 2 wherein a vibrator is provided at the center of a circle defined by said multiple circular openings and between said inner and outer hoods.

5. The health protection device for udders of cows of claim 1 or 2 wherein permanent magnets wound with coils are arranged on a back face of said inner hood and around said circular openings.

6. The health protection device for udders of cows of claim 3 wherein a vibrator is provided at the center of a circle defined by said multiple circular openings and between said inner and outer hoods.

7. The health protection device for udders of cows of claim 3 wherein permanent magnets wound with coils are arranged on a back face of said inner hood and around said circular openings.

8. The health protection device for udders of cows of claim 6 wherein permanent magnets wound with coils are arranged on a back face of said inner hood and around said circular openings.

9. The health protection device for udders of cows of claim 4 wherein permanent magnets wound with coils are arranged on a back face of said inner hood and around said circular openings.

* * * * *